(12) United States Patent
Lebreton

(10) Patent No.: US 6,207,175 B1
(45) Date of Patent: Mar. 27, 2001

(54) POWDERED COSMETIC AND/OR DERMATOLOGICAL LOTION AND ITS USE

(75) Inventor: Francoise Lebreton, Bures-sur-Yvette (FR)

(73) Assignee: L'Oreal, Paris (FR)

(*) Notice: Subject to any disclaimer, the term of this patent is extended or adjusted under 35 U.S.C. 154(b) by 0 days.

(21) Appl. No.: 09/428,986

(22) Filed: Oct. 29, 1999

(30) Foreign Application Priority Data

Nov. 4, 1998 (FR) .................................................. 98 13867

(51) Int. Cl.$^7$ ............................... A61K 7/00; A61K 7/02; A61K 7/06

(52) U.S. Cl. ..................... 424/401; 424/70.1; 424/70.11; 424/70.16; 424/62; 424/63; 514/844; 514/845; 514/846

(58) Field of Search .................................... 424/401, 70.1, 424/70.11, 70.16, 62, 63; 514/844–847

(56) References Cited

U.S. PATENT DOCUMENTS

| | | | |
|---|---|---|---|
| 5,053,221 | * | 10/1991 | Robertson et al. .................... 424/63 |
| 5,593,680 | * | 1/1997 | Bara et al. ........................... 424/401 |
| 5,955,091 | * | 9/1999 | Hansenne ............................. 424/401 |

FOREIGN PATENT DOCUMENTS

| | | |
|---|---|---|
| 0 447 286 | 9/1991 | (EP) . |
| 0 447 287 | 9/1991 | (EP) . |
| 0 486 394 | 5/1992 | (EP) . |
| 0 566 442 | 10/1993 | (EP) . |
| 0 692 237 | 1/1996 | (EP) . |
| 0 770 373 | 5/1997 | (EP) . |
| 2 238 242 | 5/1991 | (GB) . |

* cited by examiner

Primary Examiner—Gollamudi S. Kishore
Assistant Examiner—Liliana Di Nola-Baron
(74) Attorney, Agent, or Firm—Oblon, Spivak, McClelland, Maier & Neustadt, P.C.

(57) ABSTRACT

A cosmetic and/or dermatological lotion comprising an aqueous phase and a powdered phase, the powdered phase comprising at least one active powder and hollow particles based on at least one acrylic or methacrylic polymer or copolymer, the aqueous phase being present in an amount ranging from 90 to 99.99% by weight with respect to the total weight of the lotion. The inventive lotion has the advantage of being soft on application and of exhibiting a powdered phase which does not become clogged. The lotion may be used for caring for, cleaning, removing make-up from and/or coloring the skin, mucous membranes and/or scalp.

24 Claims, No Drawings

POWDERED COSMETIC AND/OR DERMATOLOGICAL LOTION AND ITS USE

BACKGROUND OF THE INVENTION

1. Field of the Invention

The present invention relates to a cosmetic and/or dermatological lotion comprising an aqueous phase and a powdered phase, the powdered phase comprising at least one active powder and hollow particles based on at least one acrylic or methacrylic polymer or copolymer, and the use of the said lotion in caring for, cleaning, removing make-up from and/or coloring the skin, mucous membranes and/or scalp.

The present invention also relates to the use of hollow particles based on at least one acrylic or methacrylic polymer or copolymer in a cosmetic and/or dermatological lotion comprising an aqueous phase and a powdered phase comprising at least one active powder for preventing the powdered phase from becoming clogged and for conferring, on the lotion, softness on application on the skin, mucous membranes and/or scalp.

2. Discussion of the Background

Cleaning of the skin is very important in caring for the face. Cleaning should be as effective as possible because fatty residues, such as excess sebum, residues from cosmetic and/or dermatological products used daily and make-up products, in particular waterproof products, accumulate in the skin folds and at the surface of the skin and can block the pores of the skin and lead to the appearance of spots. Poor quality cleaning or make-up removal is often responsible, among other causative factors, for a muddy complexion.

The use is known, in the field of caring for, cleaning and removing make-up from human skin, of powdered lotions or tonics, that is to say compositions comprising two phases: an aqueous phase, optionally with alcohol added, and a phase composed of an active powder, that is to say a powder which is effective with regard to the skin, for example in terms of removing sebum or of having a mattifying effect. In the bottle, these two phases are separated when the product is at rest and they must be mixed at the time of use by agitating. After standing for a few hours, they again separate into two phases, resuming their original condition.

JP 9-48721 discloses a lotion comprising an aqueous/ethanolic phase and a porous or water-absorbing powder, such as starch powder or silicic acid anhydride powder. These lotions can be us ed to remove excess sebum from the skin and to absorb dirt.

However, the use of a powdered lotion may have disadvantages. This is because the separation by settling after use is often lengthy and incomplete, the consequence of which is that the aqueous or aqueous/alcoholic phase is not clear and therefore has an appearance which causes a potential user to reject the product. In addition, the powdered phase has a tendency to become clogged at the bottom of the bottle and t o form a "cake", which often makes it difficult to resuspend the powder during use.

The addition of silica is known in order to limit this clogging effect. However, the addition of silica has the disadvantage of giving a rough nature to the lotion, which is unpleasant for the user.

The need therefore remains for a powdered lotion which does not have the disadvantages of the compositions described above and which in, particular, has a powdered phase which does not become clogged, while being soft on application.

SUMMARY OF THE INVENTION

It is an object of the invention to provide a powdered lotion. It is another object of the invention to provide a powdered lotion which does not suffer from the clogging disadvantages described above.

It is another object of the invention to provide a powdered lotion which may be used for caring for, cleaning, removing make-up from and/or coloring the skin, mucous membranes and/or scalp.

The present inventors have found, surprisingly, that the addition of hollow particles based on at least one acrylic or methacrylic polymer or copolymer to powdered lotions makes it possible to avoid the phenomenon of clogging while giving great softness on application to the lotion.

Accordingly, the objects of the invention, and others, may be accomplished with a lotion composition suitable for cosmetic and/or dermatological use, comprising:

90 to 99.99% by weight, with respect to the total weight of the lotion, of an aqueous phase; and a powdered phase comprising at least one active powder and hollow particles comprised of at least one acrylic or methacrylic polymer or copolymer.

The phrase "aqueous phase" is understood to mean, in the lotion of the present invention, the liquid phase of the lotion, whether it is strictly aqueous or aqueous/alcoholic, as opposed to the powdered phase.

The inventive lotion has the advantage of exhibiting a powdered phase which does not become clogged and it makes possible a smooth treatment of the skin, mucous membranes and/or scalp.

The objects of the invention may also be accomplished with a method of caring for, cleaning, removing make-up from and/or coloring the skin, mucous membranes and/or scalp, comprising applying the inventive lotion composition to the skin, mucous membranes and/or scalp.

The objects of the invention may also be accomplished with a method of preventing the powdered phase of a lotion suitable for cosmetic and/or dermatological use, wherein the lotion comprises an aqueous phase and a powdered phase, from becoming clogged and for conferring, on the lotion, softness during application to the skin, mucous membranes and/or scalp, comprising incorporating into the lotion hollow particles comprised of least one acrylic or methacrylic polymer or copolymer.

A more complete appreciation of the invention and many of the attendant advantages thereof will be readily obtained as the same becomes better understood by reference to the following detailed description.

DETAILED DESCRIPTION OF THE INVENTION

In the context of the present invention, the word "lotion" means that the composition is liquid and therefore has a viscosity of less than 0.1 Pa·s (100 centipoises), preferably of less than 0.06 Pa·s (60 centipoises), this viscosity being measured at 25° C. with a Contraves Rheomat 108/ER device. In a particularly preferred embodiment, the lotion of the invention comprises solely an aqueous phase and a powdered phase and is therefore devoid of oils.

The lotion according to the invention is intended for a topical application and therefore comprises a physiologically acceptable medium, that is to say compatible with the skin, mucous membranes and/or scalp.

The amount of powdered phase in the lotion according to the invention may range from 0.01 to 10%, preferably from 0.2 to 8%, by weight with respect to the total weight of the lotion. These ranges include all specific values and subranges therebetween, such as 0.05, 0.1, 0.5, 1, 2, 3 and 5% by weight.

The active powder of the lotion according to the invention can be chosen from any powder commonly used in powdered lotions and which is particularly active in caring for, removing make-up from, cleaning and/or coloring the skin, mucous membranes and/or scalp. It can be, for example, a mattifying, cleaning, make-up removing, coloring, astringent, antibacterial and/or protective powder (for example, UV protection).

Examples of the active powder include, for example, kaolin, zinc oxide, polyethylene powders, polyamide powders and in particular the Nylon powders listed under the CTFA name ("International Cosmetic Ingredient Dictionary and Handbook") of "Nylon 12" or "Nylon 6", such as, for example, those sold under the name "Orgasol" by the Company Atochem, powders of vegetable origin, such as henna or sandalwood powders, titanium oxides and nanotitaniums (or nano-scale titanium oxides), iron oxides and nano-scale iron oxides, starch, or silicic acid anhydride powder. Mixture of these powders may also be used.

The amount of active powder in the lotion according to the invention preferably ranges from 0.005 to 9.5% and more preferably from 0.1 to 5% by weight with respect to the total weight of the lotion. These ranges include all specific values and subranges therebetween, such as 0.01, 0.02, 0.05, 0.2, 0.5, 1, 2, 3 and 8% by weight.

The hollow particles which are used in the lotion according to the invention may be prepared from acrylic or methacrylic acid monomers or from acrylic or methacrylic acid ester monomers, such as methyl acrylate or methacrylate, alone or by copolymerization with other monomers possessing ethylenic unsaturation, such as vinylidene chloride, acrylonitrile, styrene and its derivatives, butadiene and its derivatives, and mixtures thereof. The polymers constituting these hollow particles may or may not be cross-linked.

The internal cavity of the particles in principle comprises a gas, which can be air, nitrogen or a hydrocarbon, such as isobutane or isopentane.

Examples of hollow particles which may be used in the lotion of the invention include for example, poly(methyl methacrylate) particles, such as those sold by the company Wackherr under the name "Covabead LH 85".

The hollow particles can also be chosen from the particles of an expanded copolymer of vinylidene chloride, of acrylonitrile and of methyl methacrylate and in particular of particles of an expanded terpolymer of vinylidene chloride, of acrylonitrile and of methacrylate sold under the trade name Expancel by Nobel Casco under the references 551 DE 50 (particle size of approximately 40 μm), 551 DE 20 (particle size of approximately 30 μm and density of approximately 65 kg/m$^3$), 551 DE 12 (particle size of approximately 12 em), 551 DE 80 (particle size of approximately 80 μm) and 461 DE 50 (particle size of approximately 50 μm). Use may also be made of microspheres formed of the same expanded terpolymer, having a particle size of approximately 18 μm and a density of approximately 70 kg/m$^3$, known hereinbelow as EL 23. The terpolymer particles indicated above can be dry or hydrated and can be obtained, for example, according to the processes of Patents and Patent Applications EP-A-056,219, EP-A-348,372, EP-A-486,080, EP-A-320,473, EP-A-112,807 and U.S. Pat. No. 3,615,972, each of which is incorporated by reference. A mixture of these various particles described above may also be used.

The hollow particles of the invention preferably have a particle size ranging from 1 μm to 100 μm and more preferably ranging from 5 μm to 80 μm. These ranges include all specific values and subranges therebetween, such as 2, 3, 8, 10, 25, 50 and 75 μm.

According to a preferred embodiment of the invention, use is made, as hollow particles, of poly(methyl methacrylate) particles, which have the advantage of making possible faster separation by settling of the aqueous and powdered phases after agitation.

The hollow particles of the lotion according to the invention are present in concentrations preferably ranging from 0.005 to 9.5% and more preferably from 0.1 to 5% by weight with respect to the total weight of the lotion. These ranges include all specific values and subranges therebetween, such as 0.01, 0.02, 0.05, 0.2, 0.5, 1, 2 and 7% by weight.

As indicated above, the phrase "aqueous phase" is understood to mean, in the lotion according to the invention, the liquid phase of the lotion, as opposed to the powdered phase. This aqueous phase can be entirely composed of water or can be aqueous/alcoholic, that is to say have one or more water-miscible solvents, such as a primary alcohol(s), added to it.

The aqueous phase of the lotion according to the invention represents from 90 to 99.99% and preferably from 92 to 99.8% by weight with respect to the total weight of the lotion. These ranges include all specific values and subranges therebetween, such as 91, 93, 94, 95, 96, 97, 98 and 99% by weight. The aqueous phase preferably comprises at least 40% and better still at least 50% by weight of water with respect to the total weight of the lotion.

The aqueous phase may also contain a primary alcohol. Examples include aliphatic alcohol with a linear or branched chain comprising from 1 to 6 carbon atoms and preferably from 2 to 4 carbon atoms. Mention may be made, as primary alcohol, of, for example, ethanol, propanol and isopropanol. Ethanol or of a mixture of ethanol and of another primary alcohol, such as isopropanol, is preferred.

When the lotion comprises one or more primary alcohols, the amount of primary alcohol(s) can vary within a wide range according to the purpose anticipated for the lotion according to the invention. It can range, for example, from 0.01 to 55% and preferably from 0.1 to 40% by weight with respect to the total weight of the lotion. These ranges include all specific values and subranges therebetween, such as 0.05, 0.5, 1, 2, 5, 10, 25 and 40% by weight.

The aqueous phase can also comprise other additives commonly used in this type of lotion and in particular one or more polyols, such as glycerol, ethylene glycol, propylene glycol, butylene glycol, dipropylene glycol, polyglycerols, such as diglycerol, triglycerol and tetraglycerol, sorbitol, sugars and their mixtures.

The lotion according to the invention can comprise an amount of polyol(s) ranging, for example, from 0.01 to 20% and preferably from 0.1 to 10% by weight with respect to the total weight of the lotion. These ranges include all specific values and subranges therebetween, such as 0.02, 0.05, 0.2, 0.5, 1, 2, 3, 5, 10 and 15% by weight.

The water of the aqueous phase can be pure or demineralized water. However, a portion of the water used in the compositions according to the invention can optionally be chosen from mineral or thermal waters. In general, a mineral water is fit for consumption, which is not always the case with a thermal water. Each of these waters comprises, inter alia, dissolved minerals and trace elements. These waters are known to be employed for specific treatment purposes, depending on the specific trace elements and minerals which they comprise, such as moisturization and desensitization of the skin or the treatment of certain dermatoses. The term "mineral or thermal waters" will be understood to denote not only natural mineral or thermal waters but also natural mineral or thermal waters enriched in additional mineral and/or trace element constituents, as well as aqueous mineral and/or trace-element solutions prepared from purified water (demineralized or distilled water).

A natural thermal or mineral water used according to the invention can, for example, be chosen from water from Vittel, waters from the Vichy basin, water from Uriage, water from La Roche Posay, water from La Bourboule, water from Enghien-les-Bains, water from Saint Gervais-les-Bains, water from Neris-les-Bains, water from Allevard-les-Bains, water from Digne, water from Maizieres, water from Neyrac-les-Bains, water from Lons-le-Saunier, water from Eaux-Bonnes, water from Rochefort, water from Saint Christau, water from Fumades, water from Tercis-les-Bains, water from Uriage-les-Bains and water from Avene.

The lotions of the invention can additionally comprise water-soluble adjuvants used in the cosmetics and/or dermatological field, such as preservatives, antioxidants, fragrances, screening agents, coloring materials or hydrophilic active principles. Mention may be made, as active principles, of, for example, vitamins, such as panthenol, derivatives of vitamins and in particular their esters, antibacterial agents, lightening or whitening agents, moisturizers, keratolytic agents, such as α-hydroxy acids, soothing agents, or toning agents, such as plant extracts, for example ruscus extract.

The lotion of the invention can constitute in particular a lotion for caring for, cleaning, removing make-up from and/or coloring the skin, mucous membranes and/or scalp.

Another subject-matter of the invention is therefore the cosmetic use of the lotion as defined above for caring for, cleaning, removing make-up from and/or coloring the skin, mucous membranes and/or scalp.

The lotion of the invention is also be suitable for the treatment of greasy skin.

Another subject-matter of the invention is the use of the lotion as defined above in the preparation of a composition intended for the treatment of greasy skin.

For such treatments as described above, the lotion is applied to the area desired by the user to be treated. The lotion may be applied by a variety of techniques, such as application with the finger, with an applicator pad or towel, etc. Typically, the area desired to be treated is coated with a layer of the lotion. As will be readily appreciated by those in the art, the lotion is left on the area to be treated for a time that may vary widely, as determined by the user.

EXAMPLES

Having generally described this invention, a further understanding can be obtained by reference to certain specific examples which are provided herein for purposes of illustration only and are not intended to be limiting unless otherwise specified. The amounts are indicated therein as percentages by weight.

Example 1

| Aqueous phase: | |
| --- | --- |
| Ethanol | 15% |
| Glycerol | 5% |
| Panthenol | 1% |
| Ruscus extract | 0.1% |
| Preservatives | q.s. |
| Fragrance | q.s. |
| Water | q.s. to 100% |
| Powdered phase | |
| Kaolin | 1% |
| Zinc oxide | 0.3% |
| Covabeads LH-85 | 1% |

The lotion is prepared by mixing the following constituents of the aqueous phase: glycerol, panthenol, ruscus extract, preservatives and water, by adding the ethanol, in which the fragrance is dissolved, thereto and by then incorporating the powders therein one by one.

A lotion is obtained which separates very easily on settling and which has a powdery phase which does not exhibit clogging. It is very soft on application and is capable of caring for the skin and in particular of moisturizing it and toning it up.

Example 2

| Aqueous phase | |
| --- | --- |
| Ethanol | 35% |
| Butylene glycol | 5% |
| Preservatives | q.s. |
| Fragrance | q.s. |
| Water | q.s. to 100% |
| Powdered phase | |
| Orgasol | 0.3% |
| Expancel 551 DE 50 | 0.5% |

The lotion is prepared by mixing the following constituents of the aqueous phase: butylene glycol, preservatives and water, by adding the ethanol, in which the fragrance has been dissolved, thereto and by then incorporating the powders therein one by one.

A lotion is obtained which separates easily on settling and which has a powdery phase which does not exhibit clogging. It makes possible good cleaning of the skin while being very soft on application.

Obviously, numerous modifications and variations of the present invention are possible in light of the above teachings. It is therefore to be understood that within the scope of the appended claims, the invention may be practiced otherwise than as specifically described herein.

The present application is based on French Patent Application Serial No. 98-13867, filed on Nov. 4, 1998, and incorporated herein by reference in its entirety.

What is claimed is:

1. A lotion composition having a viscosity of 0.1 Pa.s or less suitable for cosmetic and/or dermatological use, consisting essentially of:
    90 to 99.99% by weight, with respect to the total weight of the lotion, of an aqueous phase; and
    a powdered phase comprising at least one active powder and hollow particles comprised of at least one acrylic or methacrylic polymer or copolymer.

2. The lotion composition of claim 1, wherein the active powder is a powder which is active in caring for, removing make-up from, cleaning and/or coloring the skin, mucous membranes and/or scalp.

3. The lotion composition of claim 1, wherein the active powder is selected from the group consisting of mattifying, cleaning, make-up removing, coloring, astringent, antibacterial and protective powders.

4. The lotion composition of claim 1, wherein the active powder is selected from the group consisting of kaolin, zinc oxide, polyethylene powders, polyamide powders, powders of vegetable origin, titanium oxides and nanotitaniums, iron oxides, nano-scale iron oxides, starch, silicic acid anhydride powder and their mixtures.

5. The lotion composition of claim 1, which comprises from 0.005 to 9.5% by weight of active powder with respect to the total weight of the lotion.

6. The lotion composition of claim 1, wherein the hollow particles are the reaction products of the polymerization acrylic or methacrylic acid monomers or from acrylic or methacrylic acid ester monomers, alone or by copolymerization with other monomers possessing ethylenic unsaturation.

7. The lotion composition of claim 1, wherein the hollow particles are selected from the group consisting of poly (methyl methacrylate) particles, particles of an expanded terpolymer of vinylidene chloride, of acrylonitrile and of methacrylate, and mixtures thereof.

8. The lotion composition of claim 1, wherein the hollow particles have a particle size ranging from 1 $\mu$m to 100 $\mu$m.

9. The lotion composition of claim 1, wherein the hollow particles have a particle size ranging from 5 $\mu$m to 80 $\mu$m.

10. The lotion composition of claim 1, which comprises from 0.005 to 9.5% by weight of hollow particles, with respect to the total weight of the lotion.

11. The lotion composition of claim 1, wherein the aqueous phase comprises at least 40% by weight of water, with respect to the total weight of the lotion.

12. The lotion composition of claim 1, wherein the aqueous phase comprises at least one primary alcohol.

13. The lotion composition of claim 1, wherein the primary alcohol is an aliphatic alcohol having from 2 to 4 carbon atoms.

14. The lotion composition of claim 12, wherein the amount of primary alcohol(s) ranges from 0.01 to 55% by weight with respect to the total weight of the lotion.

15. The lotion composition of claim 1, wherein the aqueous phase comprises at least one polyol.

16. The lotion composition of claim 15, wherein the polyol is selected from the group consisting of glycerol, ethylene glycol, propylene glycol, butylene glycol, dipropylene glycol, polyglycerols, sorbitol, sugars and mixtures thereof.

17. The lotion composition of claim 15, wherein the amount of polyol(s) ranges from 0.01 to 20% by weight, with respect to the total weight of the lotion.

18. The lotion composition of claim 1, which is suitable for caring for, cleaning, removing make-up from and/or coloring the skin, mucous membranes and/or scalp.

19. The lotion composition of claim 1, which has a viscosity of less than 0.1 Pa.s.

20. The lotion composition of claim 1, which is devoid of oils.

21. A method preparing the lotion composition of claim 1, comprising combining the aqueous phase and the active powder.

22. A method caring for, cleaning, removing make-up from and/or coloring the skin, mucous membranes and/or scalp, comprising applying the lotion composition of claim 1 to the skin, mucous membranes and/or scalp.

23. The method of claim 22, wherein the lotion is applied to greasy skin.

24. A method of preventing the powdered phase of a lotion suitable for cosmetic and/or dermatological use, wherein the lotion comprises an aqueous phase and a powdered phase, from becoming clogged and for conferring, on the lotion, softness during application to the skin, mucous membranes and/or scalp, comprising incorporating into the lotion hollow particles comprised of least one acrylic or methacrylic polymer or copolymer.

* * * * *

UNITED STATES PATENT AND TRADEMARK OFFICE
CERTIFICATE OF CORRECTION

PATENT NO. : 6,207,175 B1
DATED : March 27, 2001
INVENTOR(S) : Francoise Lebreton Page 1 of 1

It is certified that error appears in the above-identified patent and that said Letters Patent is hereby corrected as shown below:

Column 6,
Line 60, "Pa.s" should be -- Pa·s --.

Column 8,
Line 20, "Pa.s" should read -- Pa·s --.

Signed and Sealed this

Eleventh Day of September, 2001

*Attest:*

NICHOLAS P. GODICI
*Acting Director of the United States Patent and Trademark Office*

*Attesting Officer*